United States Patent
Lu et al.

[11] Patent Number: 5,951,593
[45] Date of Patent: Sep. 14, 1999

[54] APPARATUS FOR PREVENTING ATRIAL FIBRILLATION USING PRECURSORS

[76] Inventors: Richard Lu, 1820 Via Petirrato, #E, Thousand Oaks, Calif. 91320; Albert Dawson, 491 W. Jamison Pl., Littleton, Colo. 80120; Saul Greenhut, 3586 S. Waco St., Aurora, Colo. 80013; Bruce Steinhaus, 8120 W. Mountain Shadows, Flasgstaff, Ariz. 86001

[21] Appl. No.: 08/920,836

[22] Filed: Aug. 29, 1997

[51] Int. Cl.⁶ .................................................. A61N 1/362
[52] U.S. Cl. .............................................................. 607/14
[58] Field of Search .................... 607/4, 14, 15, 607/5

[56] References Cited

U.S. PATENT DOCUMENTS

| | | | |
|---|---|---|---|
| 4,543,963 | 10/1985 | Gessman | 607/14 |
| 4,572,192 | 2/1986 | Jackman et al. | 607/14 |
| 4,577,633 | 3/1986 | Berkovits et al. | 607/15 |
| 5,205,283 | 4/1993 | Olson | 607/14 |
| 5,486,199 | 1/1996 | Kim et al. | 607/5 |
| 5,509,925 | 4/1996 | Adams et al. | 607/5 |

*Primary Examiner*—William E. Kamm
*Attorney, Agent, or Firm*—Gottlieb, Rackman & Reisman, P.C.

[57] ABSTRACT

An implanted pacemaker senses intrinsic atrial events and generates corresponding pacing pulses. The atrial events are also monitored for a precursor of an atrial fibrillation episode. If such a precursor is detected, the pacemaker generates therapy designed to prevent the atrial fibrillation episode. For example, the atrium and/or the ventricle may be overdriven at a pacing rate above the intrinsic rate.

39 Claims, 7 Drawing Sheets

APPARATUS FOR PREVENTING ATRIAL FIBRILLATION USING PRECURSORS

BACKGROUND OF THE INVENTION a. Field of Invention

This invention pertains to an implantable pacemaker and more particularly to a pacemaker constructed and arranged to recognize the imminent onset of atrial fibrillation and to automatically take steps necessary for the prevention thereof. The invention further pertains to a method of detecting and preventing atrial fibrillation within an implantable pacemaker.

b. Description of the Prior Art

Since ventricular tachyarrhythmia can have grave and potentially lethal consequences, the primary concern for clinicians until recently has been the detection and reversion of this undesirable condition. While many pacemakers were also capable of detecting atrial fibrillation, this latter condition was believed to be relatively benign, if unpleasant to the patient. Accordingly, atrial fibrillation was either ignored, or treated in a palliative manner.

However, since present pacemakers are capable of treating ventricular arrhythmia rather well, much attention has turned toward the detection and treatment of atrial fibrillation (AF). There are several reasons why it is thought to be important to control atrial fibrillation. First, atrial fibrillation is associated with the loss of AV synchrony and therefore can result in irregular heart rate and a hemodynamically inefficient cardiac operation. Atrial fibrillation has also been associated with other problems such as dyspnea, fatigue, vertigo, angina pectoris, and palpitations. These conditions lead to a patient losing his ability to enjoy life and to function normally, and may limit his capability to perform work and earn a living. An especially dire consequence of atrial fibrillation is stroke which is caused by an embolism originating because of blood pooling and clotting in the left atrium.

Recent studies have shown in fact that atrial fibrillation occurs in 0.3–0.4% of the general population. Moreover, the incidence of atrial fibrillation increases with age, so that it may reach 2–4% by the age of 60, and 8–11% after the age of 75 years. However until now, the only way for pacemakers to handle atrial fibrillation, if at all, was to mode switch from dual-chamber to ventricular pacing after atrial fibrillation was detected. However, this approach requires that atrial fibrillation occur in the first place. Once atrial fibrillation sets in, its undesirable effects will be felt by the patient, and provide unnecessary stress to the heart, at least until it is reverted. Moreover, once atrial fibrillation sets in, it must be reverted relatively quickly, before it can cause the formation of emboli or other complications. Also, it has been shown that the longer a subject remains in atrial fibrillation, the more likely they are to remain in atrial fibrillation and have repeated episodes.

OBJECTIVES AND SUMMARY OF THE INVENTION

In view of these disadvantages, it is an objective of the present invention to provide an implantable pacemaker which can detect events which are indicative of an imminent atrial fibrillation episode before the AF occurs.

A further objective is to provide a pacemaker which can take automatic preventive steps to insure that atrial fibrillation does not occur.

A further objective is to provide a pacemaker with continued atrial fibrillation prevention for a predetermined duration once it is started to insure that the atrial fibrillation does not recur.

Other objectives and advantages of the invention shall become apparent from the following description. Briefly, a pacemaker constructed in accordance with this invention includes a sensor for sensing intrinsic atrial activity, a pacing generator for generating pacing pulses for both the atrium and the ventricle in accordance with pacing commands and a controller for generating said commands in a manner selected to insure that the patient's heart is operating optimally. Importantly, the pacemaker is further provided with a detector for detecting events which are indicative of imminent atrial fibrillation. The detector may, for example, detect recurring atrial events which, either by their timing relative to a total atrial refractory period, or based on their morphology, can be classified as ectopic events.

Once imminent atrial fibrillation is predicted, the pacemaker automatically switches to a mode in which either one or both the atrium and the ventricle are overdriven slightly thereby preventing the atrial fibrillation episode from occurring.

After a predetermined period, the pacemaker reverts to normal operation.

The invention may also be incorporated in other cardioversion devices, such as, for example a defibrillator.

DETAILED DESCRIPTION OF THE INVENTION

A pacemaker constructed in accordance with this invention is shown in FIGS. 1–4 FIG. 1 shows a block diagram of the pacemaker. The pacemaker 10 is designed to be implanted in a patient and is connected by leads 12 and 13 to a patient's heart 11 for sensing and pacing the heart 11 as described for example in U.S. Pat. No. 5,441,523 by Tibor A. Nappholz et al., entitled FORCED ATRIOVENTRICULAR SYNCHRONY DUAL CHAMBER PACEMAKER, incorporated herein by reference. Briefly, the atrial cardiac lead 12 extends into the atrium of the heart 11 and the ventricular cardiac lead 13 extends into the ventricle of the heart 11. Leads 12 and 13 are used for both sensing electrical activity in the heart and for applying pacing pulses to the heart. The pacemaker 10 includes a pace and sense circuit 17 for the detection of analog signals from leads 12 and 13 and for the delivery of pacing pulses to the heart; a microprocessor 19 which, in response to numerous inputs received from the pace and sense circuit 17, performs operations to generate different control and data outputs to the pace and sense circuit 17; and a power supply 18 which provides a voltage supply to the pace and sense circuit 17 and the microprocessor 19 by electrical conductors (not shown). The microprocessor 19 is connected to a random access memory/read only memory unit 121 by an address and data bus 122. A low power signal line 124 is used to provide to the microprocessor 19 a logic signal indicative of a low energy level of the power supply 18. The microprocessor 19 and the pace and sense circuit 17 are connected to each other by a number of data and control lines including a communication bus 42, an atrial sense line 45, an atrial pacing control line 46, an atrial sensitivity control bus 43, an atrial pace energy control bus 44, a ventricular sense line 49, a ventricular pace control line 50, a ventricular sensitivity control bus 47, and a ventricular pacing energy control bus 48.

Figure 1:
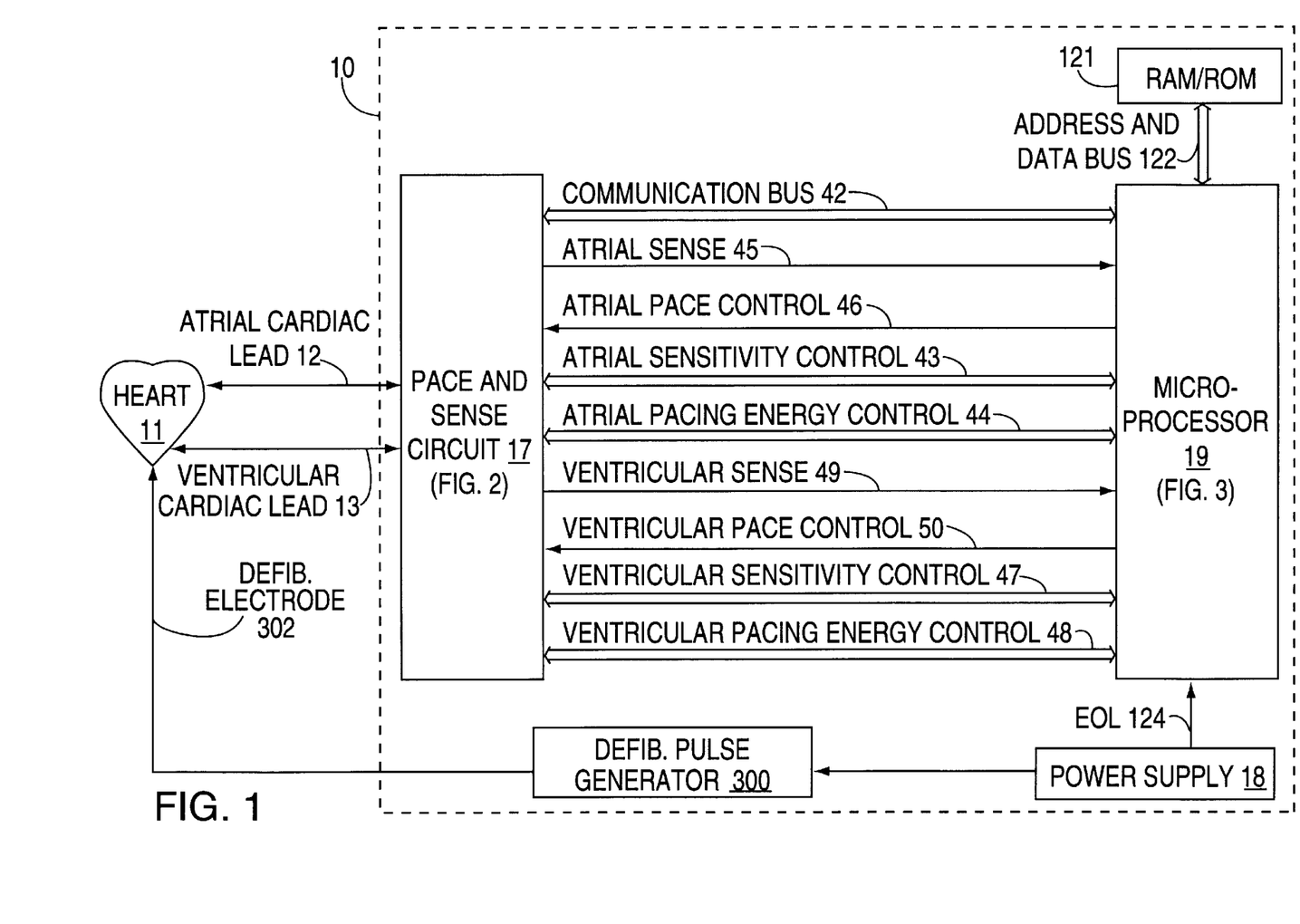
FIG. 1 shows a block diagram of a pacemaker constructed in accordance with this invention.
Figure 2:
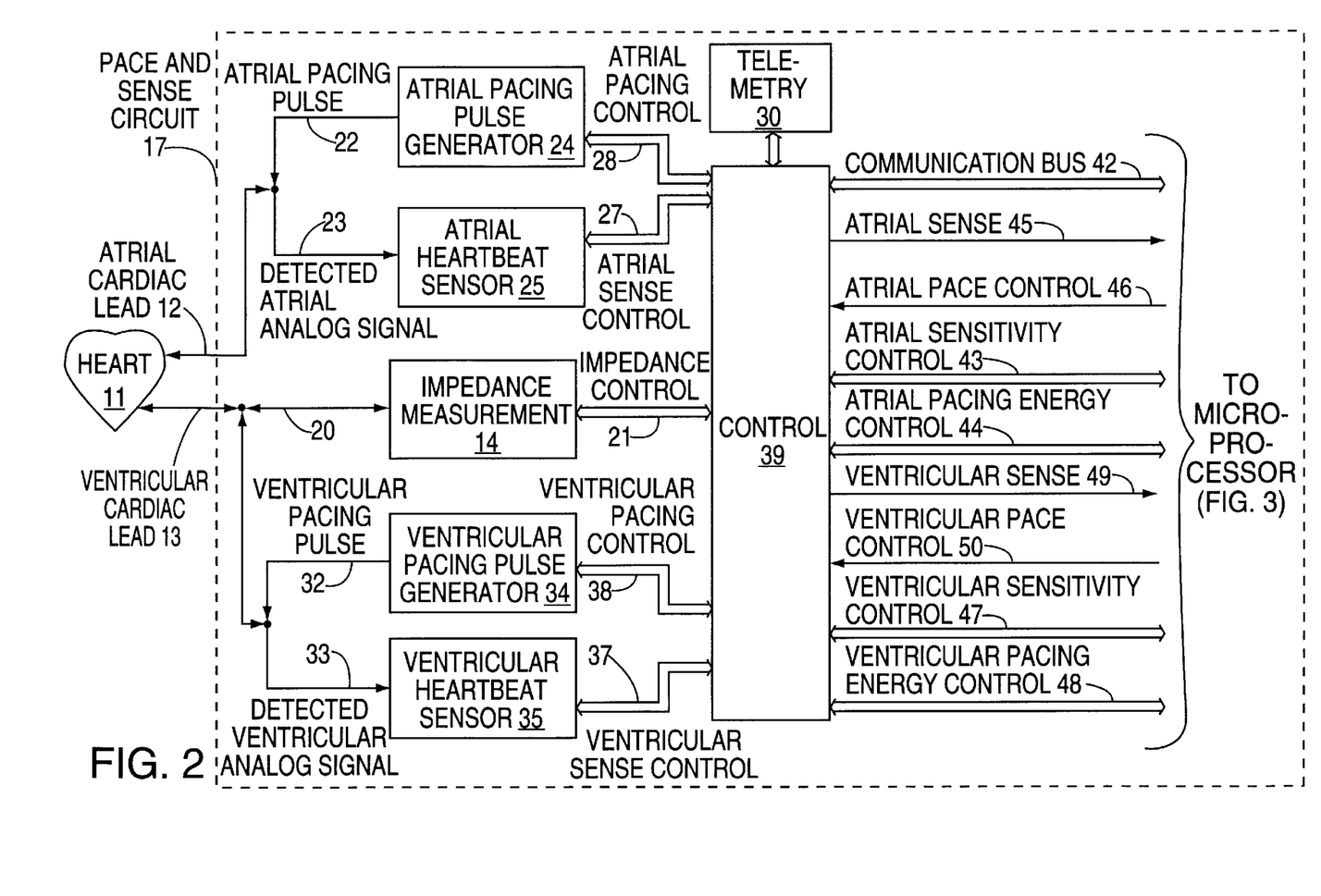
FIG. 2 shows a block diagram of the pace and sense circuit for the pacemaker of FIG. 1.

FIG. 2 shows details of the pace and sense circuit 17. The circuit 17 includes an atrial pacing pulse generator 24, a ventricular pacing pulse generator 34, an atrial heartbeat sensor 25, a ventricular heartbeat sensor 35, and a telemetry circuit 30. The preferred embodiment of the pace and sense circuit 17 also includes an impedance measurement circuit 14 for measuring a physiological parameter indicative of the patient's metabolic demand. The pace and sense circuit 17 also includes a control block 39 which is interfaced to the microprocessor 19.

In operation, the atrial and ventricular heartbeat sensor circuits 25 and 35 detect respective atrial and ventricular analog signals 23 and 33 from the heart 11 and convert the detected analog signals to digital signals. In addition, the heartbeat sensor circuits 25 and 35 receive an input atrial sense control signal on a control bus 27 and an input ventricular sense control signal on a control bus 37, respectively, from the control block 39. These control signals are used to set the sensitivity of the respective sensors.

The atrial pacing pulse generator circuit 24 receives from the control block 39, via an atrial pacing control bus 28, an atrial pace control signal and an atrial pacing energy control signal to generate an atrial pacing pulse 22 at appropriate times. Similarly, the ventricular pacing pulse generator circuit 34 receives from the control block 39, via a ventricular pacing control bus 38, a ventricular pace control signal and a ventricular pacing energy control signal to generate a ventricular pacing pulse 32. The atrial and ventricular pace control signal determine the respective timing of atrial and ventricular pacing that takes place, while the atrial and ventricular pacing energy control inputs determine the respective magnitudes of the pulse energies.

The pacemaker 10 makes an impedance measurement when the microprocessor 19 sends a signal on the impedance control bus 21 to activate the impedance measurement circuit 14. The impedance measurement circuit 14 then applies a current to the ventricular cardiac lead 13 via lead 20 and measures a voltage resulting from the applied current. These current and voltage signals define an impedance characteristic of the patient's metabolic demand, and more particularly, of the instantaneous minute volume. This instantaneous minute volume is then filtered and further modified by subtracting from it a long term average value. The resulting parameter is the minute volume parameter.

The telemetry circuit 30 provides a bidirectional link between the control block 39 of the pace and sense circuit 17 and an external device such as a programmer. It allows data such as the operating parameters to be read from or altered in the implanted pacemaker. An exemplary programmer is the 9600 Network Programmer manufactured by Telectronics Pacing Systems, Inc. of Englewood, Colo., U.S.A.

Figure 3:
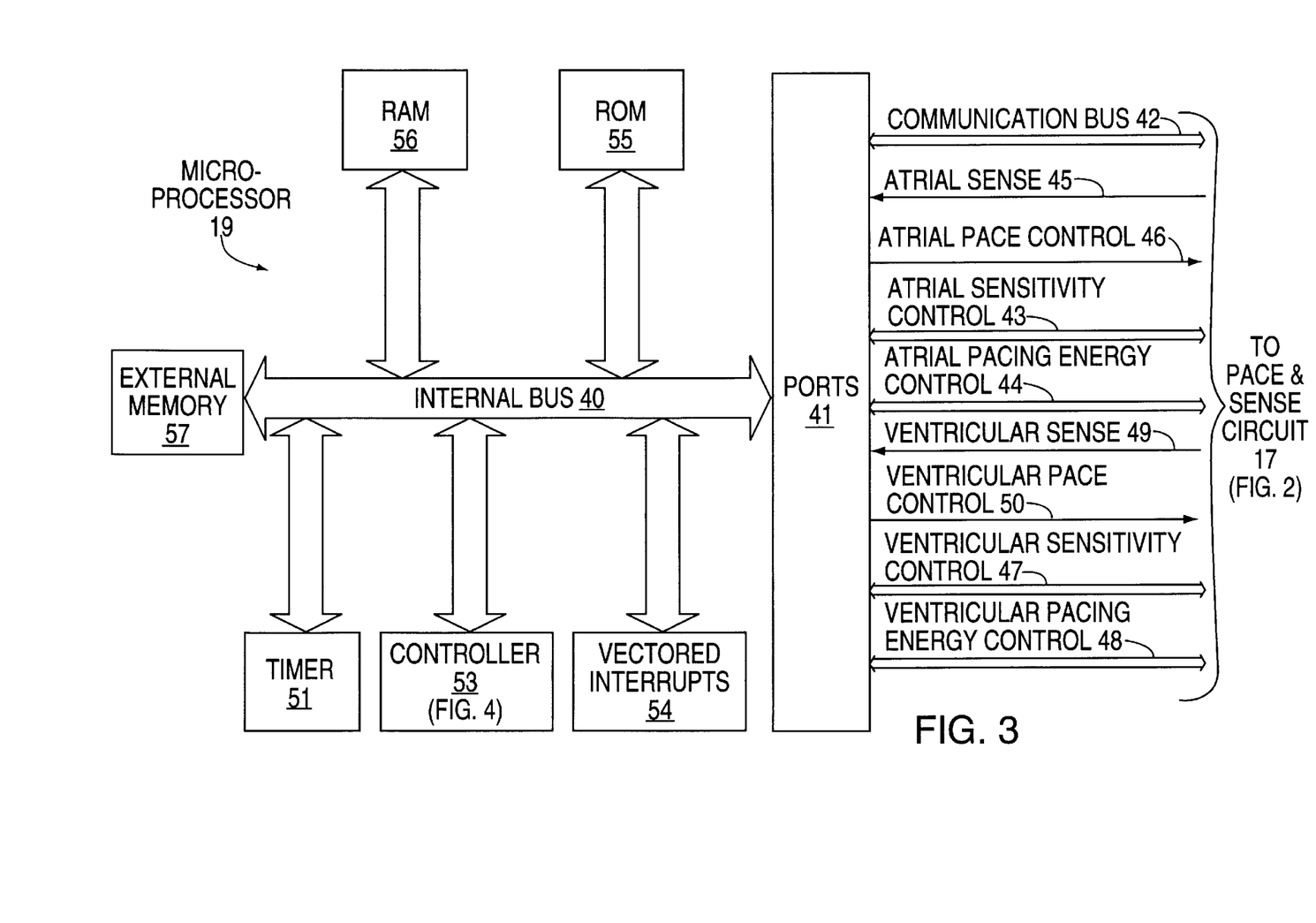
FIG. 3 shows a block diagram of a microprocessor for the pacemaker of FIG. 1.

FIG. 3 shows the microprocessor 19 having a timer circuit 51 for generating several timing signals, a controller 53, a vectored interrupts circuit 54, a ROM 55, a RAM 56, an external memory 57 and an interface port 41. Signals between these elements are exchanged via an internal communications bus 40. The RAM 56 acts as a scratchpad and active memory during execution of the programs stored in the ROM 55 and used by the microprocessor 19. ROM 55 is used to store programs including system supervisory programs, detection algorithms for detecting and confirming arrhythmias, and programming for determining the rate of the pacer, as well as storage programs for storing, in external memory 57, data concerning the functioning of the pulse generator 10 and the electrogram provided by the cardiac leads 12 and 13. The timer circuit 51, and its associated control software, implements some timing functions required by the microprocessor 19 without resorting entirely to software, thus reducing computational loads on, and power dissipation by, the controller 53.

Signals received from the telemetry circuit 30 permit an external programmer (not shown) to change the operating parameters of the pace and sense circuit 17 by supplying appropriate signals to the control block 39. The communication bus 42 serves to provide signals indicative of such control to the microprocessor 19.

The microprocessor 19 through its port 41 receives status and/or control inputs from the pace and sense circuit 17, including the sense signals on the sense lines 45 and 49 previously described. Using controller 53, it performs various operations, including arrhythmia detection, and produces outputs, such as the atrial pace control on the line 46 and the ventricular pace control on the line 50, which determine the type of pacing that is to take place. Other control outputs generated by the microprocessor 19 include the atrial and ventricular pacing energy controls on the buses 44 and 48, respectively, which determine the magnitude of the pulse energy, and the atrial and ventricular sensitivity controls on the buses 43 and 47, respectively, which set the sensitivities of the sensing circuits. The rate of the atrial and/or ventricle pacing is adjusted by controller 53 as set forth below.

The pacemaker 10 of the present invention will function properly using any metabolic indicator rate system, so long as that system is able to reliably relate the sensed parameter to an appropriate matching of metabolic demand with the paced rate. The preferred embodiment of the invention employs the impedance measurement circuit 14, shown in FIG. 2, which measures the transthoracic impedance to determine the respiratory minute volume as described in U.S. Pat. No. 4,901,725 to T. A. Nappholz, et al., issued Feb. 20, 1990 for "Minute Volume Rate-Responsive Pacemaker", incorporated herein by reference.

Figure 4:
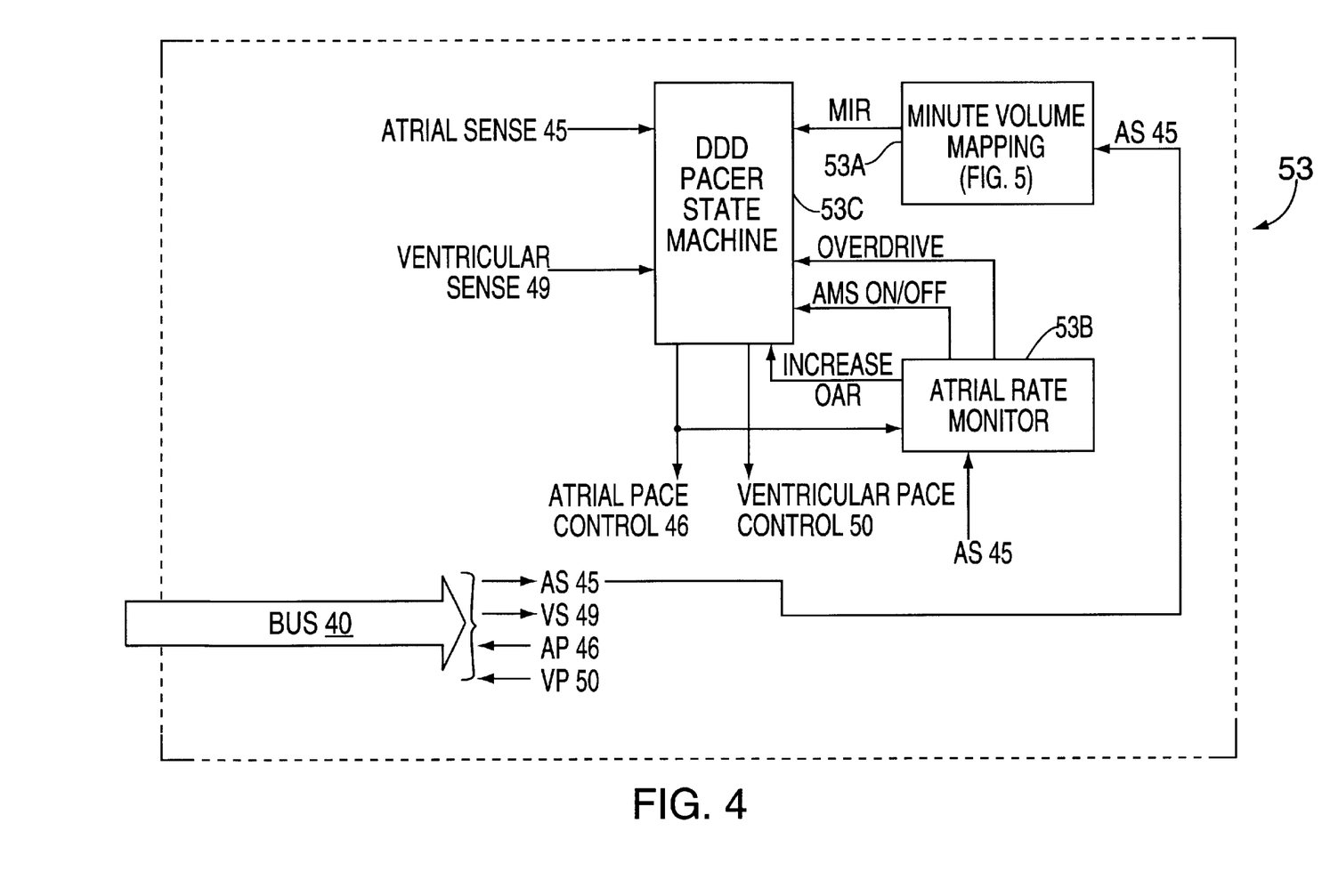
FIG. 4 shows details of the controller for the microprocessor of FIG. 3.

FIG. 4 shows the block diagram of the controller 53 of FIG. 3. The controller 53 includes a state machine 53C, a minute volume processor 53A and an atrial rate monitor 53B. The minute volume processor 53A uses the data supplied via the internal bus 40 from the impedance measurement block 14 to relate the minute volume indicated by the impedance measurement to the Metabolic Indicated Rate (MIR). This rate is then used by the state machine 53C to determine the length of each interval in the timing cycle. While the pacemaker 10 is preferably operating in a DDDR mode, it should be understood that it can operate in other modes as well. The atrial rate monitor 53B generates an Automatic Mode Switching (AMS) signal upon detection of a non-physiological atrial rate and/or rhythm. This AMS signal automatically switches the pacemaker 10 to a non-atrial tracking mode such as VVIR or DDIR. When a physiological atrial rate resumes, the AMS signal is deactivated and the pacemaker returns to an atrial tracking mode.

Controller 53 may also be used to generate commands for other cardioversion therapy. For example, in an implantable defibrillator, the controller 53 may generate defibrillation commands, as discussed more fully below.

Importantly, the atrial rate monitor 53B further detects one or more atrial fibrillation precursors such as ectopic atrial beats. If a possibly imminent atrial fibrillation event is indicated by the precursors, the monitor also sends to the state machine 53C an OVERDRIVE signal.

Figure 5:
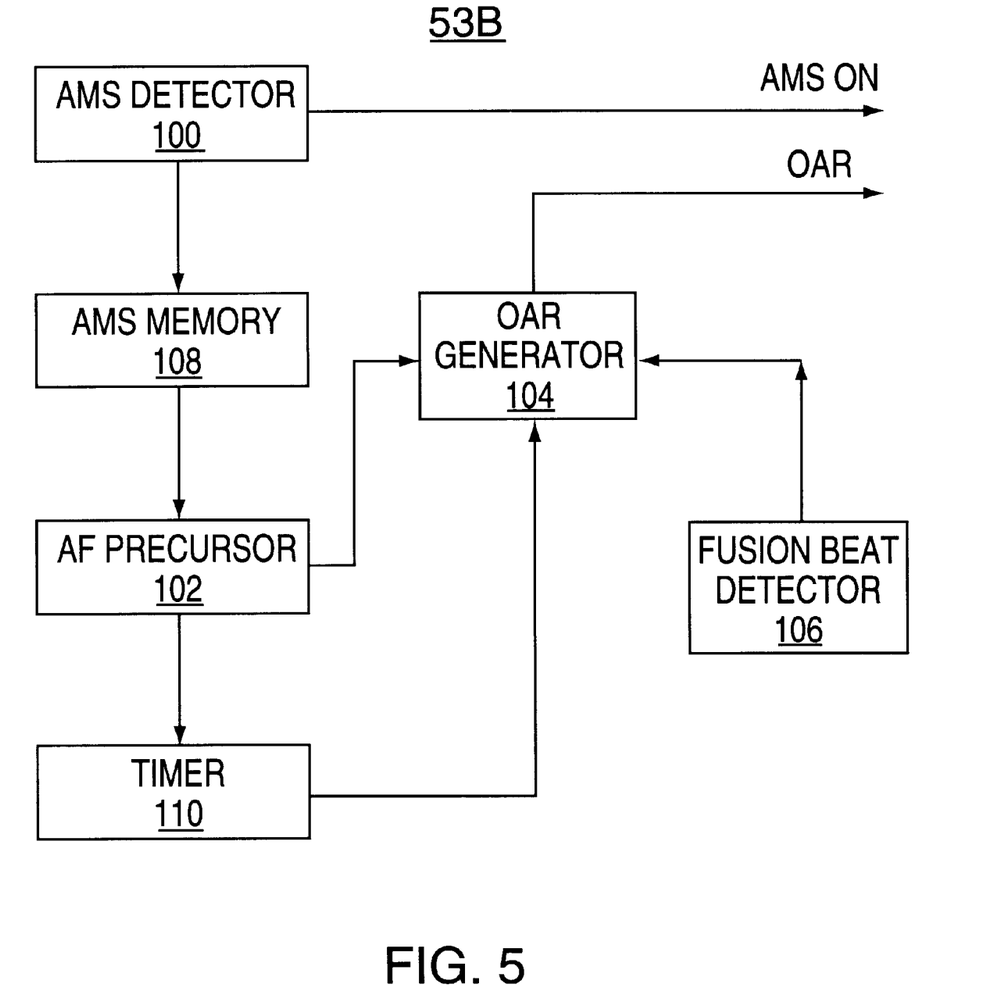
FIG. 5 shows details of the atrial rate monitor of FIG. 4.

Referring now to FIG. 5, the atrial monitor includes an AMS detector 100, an AF precursor detector 102, an OAR (overdrive atrial rate) generator 104 and an atrial fusion detector 106. The AMS detector uses any one of several known schemes for detecting atrial tachyrhythmia. For example, the AMS detector 100 may be adapted to sense an atrial event in a PVARP (post ventricular atrial refractory period).

Alternatively, an up/down counter may be used to count the number of Atrial-Atrial intervals below/above a preselected threshold. Atrial tachyarrhythmia are indicated when the counter reaches a preselected integer.

More sophisticated schemes for detecting atrial tachyarrhythmia are also known which involve morphological analysis of the atrial sensed signal.

Independently of which scheme is being used, once an atrial tachyarrhythmia is detected, the AMS detector 100 generates an AMS signal for the state machine causing the same to switch to a mode of operation wherein the ventricle is paced independently and asynchronously of the atrial events. After the atrial fibrillation ends, the AMS signal is disabled and the state machine returns to its previous pacing mode, such as DDDR.

Every AMS signal is also provided to an AMS memory which logs the frequency and duration of these AMS episodes.

Figure 6:
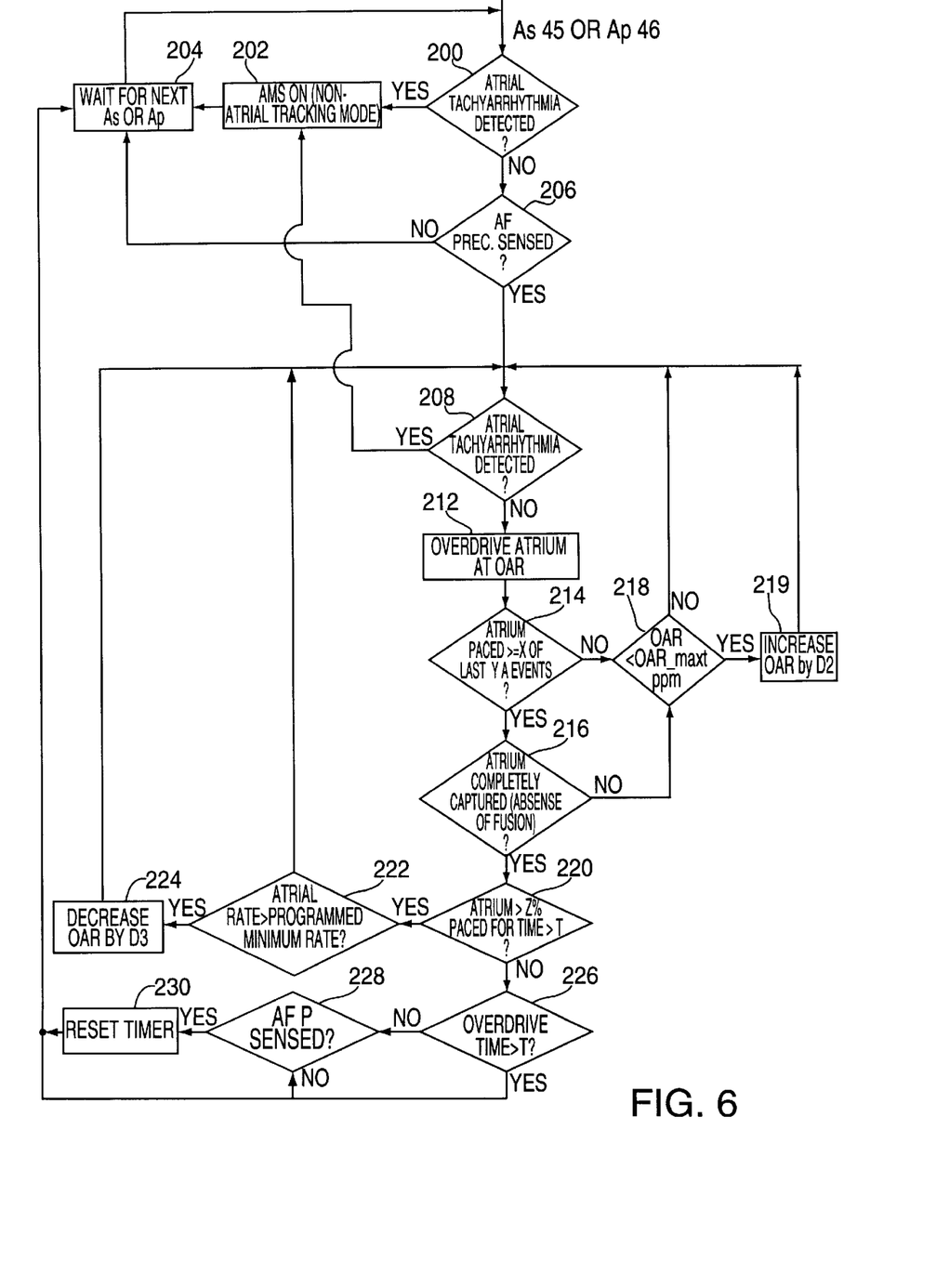
FIG. 6 shows a flow chart for the operation of the atrial rate monitor of FIG. 5.

The operation of the circuit of FIG. 5 shall now be described in conjunction with the flow chart of FIG. 6. In step 200, the AMS detector 100 detects atrial tachyarrhythmia as discussed above. If an atrial tachyarrhythmia is detected then in step 202 the AMS ON signal is activated and logged in memory 108 and the system then waits for the next atrial sense (As or Ap) event (step 204).

If no atrial tachyarrhythmia is detected in step 200, then in step 206, the atrial fibrillation precursor (AFP) detector is used to detect an atrial fibrillation precursor. Details of some embodiments of this detector are discussed below in conjunction with the description of FIGS. 7–10.

If an AF precursor is not detected in step 206, then in step 204 the system waits for the next atrial sense (As) or atrial pace signal (Ap).

If an AF precursor is detected then an AF prevention scheme is initiated as follows. First, in step 208 the atrium is checked again to confirm that atrial tachyarrhythmia has not been detected. If it has then the system reverts to step 202.

If atrial tachyarrhythmia is not detected, then in step 212, a command is generated to overdrive the atrium at a rate OAR. This rate is generated by OAR generator 104 by selecting the smaller of a preprogrammed OAR maximum limit (OAR_max) and the last normal atrial pacing rate (i.e. prior to step 206) incremented by an amount D1. D1 may be for example 5–10 ppm.

In steps 214 and 216 tests are performed to determine if the rate OAR is too slow. In step 214 a test is performed to determine if at least the last X of Y (for example 7 of 8) atrial events were paced. If yes then in step 216 a test is performed to determine if the atrium is completely captured. Capture detection may be accomplished for example by detection of the paced or fusion beat by circuit 106. Paced and fusion beats can be detected for example using PDI (paced depolarization integral) as described in U.S. Pat. No. 4,766,901.

If either test (214 or 216) is negative, then in step 218 a test is performed to determine whether the current rate has reached an upper limit OAR_max. OAR_max may be about 100 ppm. If this rate has been reached then overdriving continues by recycling to step 208. If not, then in step 219 the pacing rate is increased by an incremental amount D2 which may be 5–10 ppm.

If tests 214, 216 are positive, then in steps 220 and 222 tests are performed. The first test (step 220) is to determine if the atrium is being paced very often, for example 99% or more of the time for a predetermined period of 30 minutes or so. If so then, a second test is performed in step 222 to determine if the rate OAR exceeds the minimum programmed pacing rate. If so, then in step 224 the rate OAR is decreased by an incremental amount D3. D3 may be about 5 ppm.

Finally, if the test in step 220 is negative then in step 226 the overall time (as measured by timer 110 in FIG. 5) for the overdrive is checked. Pacing the atrium at rate OAR should be preferably limited to a certain time T. For example, overdrive might be limited to 24 hours. However, this time T may be restarted, if during overdrive a new AF precursor is sensed. Thus in step 228 a test is performed to sense a new AF precursor. In the presence of such new precursor, in step 230, the timer 110 is reset.

Figure 7:
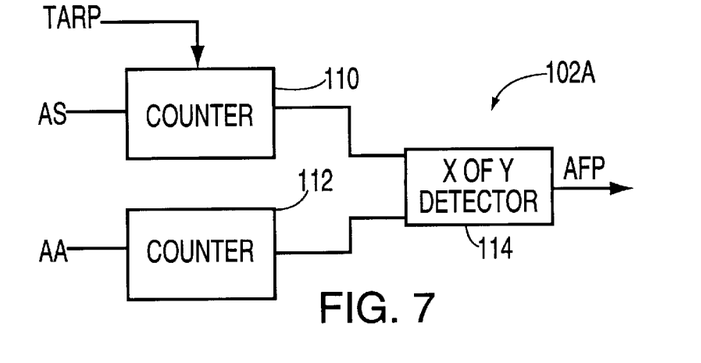
FIG. 7 shows a first embodiment of an AF precursor detector.

FIG. 7 shows a first embodiment of an AF precursor detector 102A. In this embodiment the detector 102A consists of a first counter 110, a second counter 112 and an 'X of Y' detector 114. The first counter 110 is enabled only during the total atrial refractory period (TARP) and is designed to count the number of atrial sense signals that occur during this critical period. In effect, in this embodiment any intrinsic atrial event sensed during this TARP period is considered an ectopic beat.

Counter 112 is used to count a preselected number Y of cardiac events. For example, counter 112 may be used to count AA intervals. Alternatively, any other events from the main timing sequence may be used. When the number Y is reached, the counter 112 generates a signal on its output to the X of Y detector 114. This latter detector 114 also receives an input X from counter 110. Detector 114 is designed to generate an output whenever the number from counter 110 exceeds a preselected threshold X during Y cardiac cycles. In other words, the detector 114 generates an output whenever more than X ectopic beats are detected during Y cardiac cycles. This event is indicated by the detector 114 as an AFP signal indicating that an atrial fibrillation precursor has been detected. X of Y may be for example 3 of 8.

Figure 8:
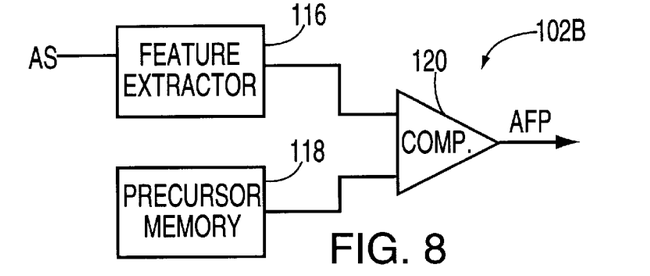
FIG. 8 shows a second embodiment of an AF precursor detector.

In the embodiment of FIG. 8, detector 102B includes a feature extractor 116, a precursor memory 118 and a comparator 120. In this embodiment, the feature extractor 116 analyzes each atrial sense signal and extracts certain morphological features such as area, minimum and maximum values, duration and so on. Memory 118 is a precursor memory used for storing features of atrial signals which are known precursors of atrial fibrillation. This information may be derived by the clinician from the patient or may be based on population results. The two sets of features from extractor 116 and memory 118 are compared by comparator 120. If the comparator 120 finds that the features of a particular atrial event (or a preselected number of atrial events) match the features of an atrial precursor within specified boundaries, then the comparator 120 generates a signal AFP indicating that an atrial fibrillation precursor has been detected.

Figure 9:
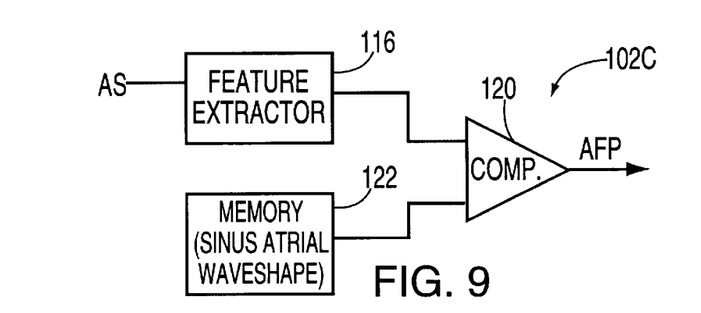
FIG. 9 shows a third embodiment of an AF precursor detector.

In the embodiment of FIG. 9 detector 102C also has the feature extractor 116 and comparator 120 but in addition, it also has a sinus memory 122. In this embodiment, memory 122 is used to store morphological features of sinus atrial intrinsic beats. These features can be collected and stored when no atrial fibrillation is observed. Comparator 120 compares the features of intrinsic sensed events as detected by extractor 116 and the features of the sinus atrial beats from memory 122. If one or more atrial events have features which do not match the features of sinus beats then an atrial fibrillation precursor signal is generated. In other words, any intrinsic signals which do not match sinus atrial beats within specified boundaries are considered ectopic beats.

Figure 10:
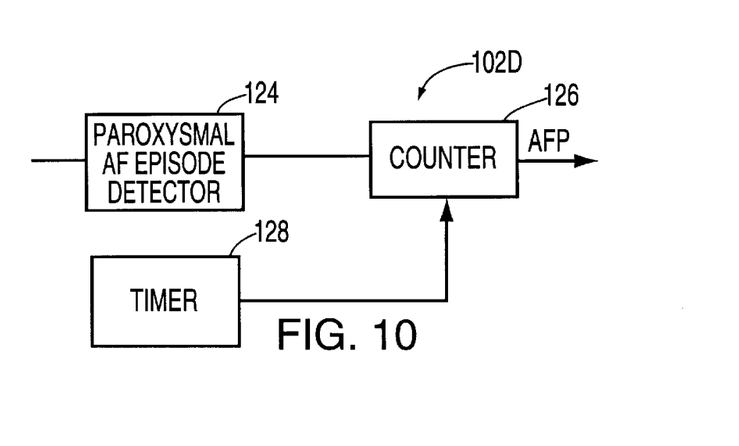
FIG. 10 shows a fourth embodiment of an AF precursor detector.

A different approach is taken in the embodiment of FIG. 10. In this embodiment, a paroxysmal atrial fibrillation detector is used to detect short episodes of AF which revert spontaneously. The detector 124 uses information from memory 108 to detect these paroxysmal episodes. These episodes are counted by a counter 126 over a predetermined time period defined by timer 128. Timer 128 may be used to define, for example, a 24 hour period. If during this period, counter 126 counts at least a predetermined number of such episodes (for example, five) then an AFP signal is generated for a predetermined time period to cause the atrium to overdrive. In this manner future atrial fibrillation episodes are prevented, or their frequency is reduced.

Thus, as set forth above, a pacemaker is presented which can detect certain events indicative of imminent atrial fibrillation, and then use this information to prevent the occurrence of this undesirable event by overdriving the atrium.

Implantable device 10 in FIGS. 1–6 is described in the preferred embodiment as an implantable pacemaker. However, the device 10 is also intended to represent other therapeutic devices for providing cardiac therapy, such as a generic implantable cardioversion device (ICD) adapted to provide antitachy- and anti-bradicardia therapy. For this embodiment, device 10 may include a defibrillation pulse generator 300 adapted to deliver defibrillating pulses via defibrillation electrode 302 in response to commands from microprocessor 19. These pulses may be used to provide atrial defibrillation, ventricular defibrillation pulses, or both.

Although the invention has been described with reference to several particular embodiments, it is to be understood that these embodiments are merely illustrative of the application of the principles of the invention. Accordingly, the embodiments described in particular should be considered exemplary, not limiting, with respect to the following claims.

We claim:

1. An implantable cardioversion device for providing therapy to a patient's heart, said device comprising:
    an atrial sensor for sensing intrinsic atrial events and generating corresponding atrial sense signals;
    an atrial tachycardia detector that detects atrial tachycardia based on said atrial events;
    a pulse generator for generating pacing pulses in response to commands;
    an atrial precursor detector for detecting a precursor indicative of an imminent atrial fibrillation episode; and
    a controller receiving said atrial sense signals and generating said commands in one of a normal and therapy mode dependent on the presence and absence of said precursor respectively, therapy being applied in said therapy mode while atrial tachycardia is not present as indicated by said atrial tachycardia detector to prevent atrial fibrillation from occurring.

2. The device of claim 1 wherein said controller is constructed to generate override commands in said therapy mode and wherein said pulse generator is responsive to said override commands to generate pacing pulses at an override rate to override the atrium.

3. The device of claim 1 wherein, said controller is constructed to generate pacing commands for said pulse generator, said pulse generator generating atrial pacing pulses in response to said pacing commands, said controller being further constructed to generate said pacing pulses at a first rate in said normal mode and at an override rate in said therapy mode; wherein said pulse generator being constructed to generate pacing pulses at said first rate in synchronism with said sensed atrial signals in said normal mode, and wherein in said therapy mode, said pulse generator is constructed to generate said pacing signals at said override rate, said override rate being selected to overdrive the atrium.

4. The device of claim 3 further comprising a capture detector constructed to detect if the atrium is captured by said pacing pulses and wherein said controller is constructed to incrementally increase said override rate if said capture detector indicates that the atrium has not been not captured.

5. The pacemaker of claim 1 wherein said precursor detector includes a paroxysmal episode detector and a counter for counting paroxysmal episodes, said precursor detector being constructed to generate said precursor signal when said counter reaches a certain value.

6. An implantable pacemaker comprising:
    an atrial sensor for sensing intrinsic atrial signals;
    a pulse generator for generating pacing pulses in response to commands;
    an atrial monitor for monitoring an intrinsic atrial rate from said intrinsic atrial signals, said atrial monitor selectively activating a mode selection signal if said atrial rate exceeds a threshold;
    an atrial precursor detector for detecting a precursor of an atrial fibrillation episode; and
    a controller for generating said commands in one of a first mode and a second mode in accordance with said mode selection signal;
    wherein said controller generates said commands signals to apply therapy selected to prevent said atrial fibrillation episode in the presence of said precursor.

7. The pacemaker of claim 6 wherein said controller is constructed to generate said command signals to define an atrial pacing rate and wherein in the presence of said precursor said controller generates said command signals to define an override atrial pacing rate, said override pacing rate being selected to exceed said intrinsic atrial rate by a differential value to overdrive the atrium.

8. The pacemaker of claim 6 wherein said precursor detector includes an ectopic detector for detecting ectopic atrial events.

9. The pacemaker of claim 8 wherein said precursor detector includes a counter for counting ectopic atrial events, said precursor being indicated when said counter reaches a predetermined value.

10. The pacemaker of claim 9 wherein said precursor is detected when said counter reaches said predetermined value during a predetermined time duration.

11. The pacemaker of claim 9 wherein said precursor is detected when said counter reaches a predetermined value during a predetermined number of cardiac cycles.

12. The pacemaker of claim 9 wherein said ectopic atrial events are atrial events sensed during a total atrial refractory period.

13. The pacemaker of claim 6 wherein said precursor detector includes a feature extractor and a comparator for comparing features of an atrial event as determined by said feature extractor and a predetermined criteria to sense said precursor.

14. The pacemaker of claim 13 wherein said precursor detector further includes a memory.

15. The pacemaker of claim 14 wherein said memory is a precursor memory used to store a preset feature characteristic of a typical ectopic atrial event.

16. The pacemaker of claim 14 wherein said memory is a sinus feature memory used to store a typical feature of a sinus atrial event.

17. The pacemaker of claim 6 wherein said precursor detector includes a paroxysmal episode detector and a counter for counting paroxysmal episodes, said precursor detector being constructed to generate said precursor signal when said counter reaches a certain value.

18. The pacemaker of claim 6 further comprising a capture detector which detects capture of the atrium by said pacing pulses wherein said pulse generator is constructed to generate in response to said commands said pacing pulses, at a rate which is increased incrementally until the atrium is captured.

19. A method of preventing atrial fibrillation using an implantable pacemaker having an atrial sensor for sensing atrial events, a pulse generator for generating pacing pulses and a precursor detector that detects a precursor of an atrial fibrillation episode, said method comprising the steps of:
   detecting a precursor of an imminent atrial fibrillation episode before the occurrence of said atrial fibrillation episode; and
   applying therapy to the heart with said pulse generator while atrial tachycardia is not present to prevent said atrial fibrillation episode.

20. The method of claim 19 wherein said therapy comprises applying atrial pacing pulses.

21. The method of claim 19 further comprising detecting an intrinsic atrial rate wherein said therapy comprises applying pacing pulses at a rate incrementally higher than said atrial intrinsic rate.

22. The method of claim 19 wherein said step of detecting said precursor comprises detecting ectopic beats in said atrium.

23. The method of claim 22 wherein said ectopic beats are detected during a total atrial refractory period.

24. The method of claim 19 wherein said step of detecting said precursor includes extracting a feature of an intrinsic event and comparing said feature to a preselected value.

25. The method of claim 24 wherein said preselected value is selected as being characteristic of typical precursors for atrial fibrillation.

26. The method of claim 24 wherein said preselected value is selected as being characteristic of sinus atrial events.

27. The method of claim 19 wherein said precursor is detected by performing morphological analysis on said intrinsic atrial events.

28. The method of claim 19 wherein said precursor is detected by sensing paroxysmal atrial events.

29. A dual chamber pacemaker for applying therapy to a patient's heart comprising:
   an atrial sensor that senses intrinsic atrial events and generates corresponding atrial sense signals;
   an atrial pacing pulse generator that generates atrial pacing pulses in response to atrial pace commends;
   a ventricular sensor that senses intrinsic ventricular activity and generates corresponding ventricular sense signals;
   a ventricular pulse generator that generates ventricular pacing pulses in response to ventricular pace commands;
   a sinus rhythm detector that detects when atrial tachycardia is not present;
   a precursor detector that detects a fibrillation precursor indicative of an imminent extended atrial episode that has not yet occurred said detector generating corresponding precursor sense indicating signals;
   a precursor therapy generator that generates therapy signals in response to precursor therapy commands selected to prevent said fibrillation before said fibrillation occurs and while atrial tachycardia is not present; and
   a controller receiving said sense signals and generating corresponding atrial pace and ventricular pace commands.

30. The pacemaker of claim 29 wherein said precursor therapy generator generates pacing pulses selected to overdrive the atrium.

31. The pacemaker of claim 29 wherein said precursor sensor includes an ectopic detector for detecting ectopic atrial events.

32. The pacemaker of claim 29 wherein said precursor sensor includes a feature extractor extracting predetermined features from said atrial sense signals and a comparator comparing said features to a predetermined criteria.

33. The pacemaker of claim 29 wherein said precursor sensor includes a paroxysmal episode detector.

34. The pacemaker of claim 33 wherein said precursor sensor further includes a counter for counting paroxysmal episodes and generating a count, said precursor sense signals being generated based on said count.

35. An implantable cardiac device comprising:
   an atrial sensor that detects a precursor for an imminent atrial fibrillation episode before said atrial fibrillation has set in and generating a precursor indication signal;
   a pulse generator responsive to a command to generate therapeutic pulses; said pulse generator being constructed to select said therapeutic pulses to prevent said episode and
   a controller for generating said command in response to said precursor indication signal.

36. The device of claim 35 further comprising a defibrillation pulse generator for generating defibrillation pulses.

37. The device of claim 36 wherein said defibrillation pulse generator generates atrial defibrillation pulses.

38. An implantable cardioversion device for providing therapy to a patient's heart, said device comprising:
   an atrial sensor for sensing intrinsic atrial events and generating corresponding atrial sense signals;

an atrial tachycardia detector that detects atrial tachycardia based on said intrinsic atrial events;

a pulse generator for generating pacing pulses in response to commands;

an atrial precursor detector for detecting a precursor, said precursor being indicative of an imminent atrial fibrillation episode; and a controller receiving said atrial sense signals and generating said commands in one of a normal mode and a therapy mode dependent on the presence and absence of said precursor respectively, said therapy mode being selected to apply therapy while atrial tachycardia is not present to prevent said atrial fibrillation episode before said atrial episode occurs.

39. An implantable pacemaker providing therapy to a patient's heart comprising:

an atrial sensor for sensing intrinsic atrial signals;

a pulse generator for generating pacing pulses in response to first and second commands;

an atrial detector that detects an intrinsic atrial rate from said intrinsic atrial signals;

an atrial precursor detector for detecting a precursor indicative of an imminent atrial fibrillation episode before the occurrence of said atrial fibrillation episode, said atrial precursor detector including a paroxysmal episode detector and a counter that counts paroxysmal episodes, said atrial precursor detector generating a precursor indicating signal when said counter reaches a predetermined value; and a controller that generates said first commands in a first mode and said second commands in a second mode, said first commands defining a first atrial rate and said second commands defining a second pacing rate, said controller being adapted to generate said second commands in response to said precursor indicating signal to apply therapy to the atrium to prevent said atrial fibrillation episode from occurring.

* * * * *